(12) United States Patent
Liu (10) Patent No.: US 11,206,986 B2
(45) Date of Patent: Dec. 28, 2021

(54) MINIATURE QUANTITATIVE OPTICAL COHERENCE ELASTOGRAPHY USING A FIBER-OPTIC PROBE WITH A FABRY-PEROT CAVITY

(71) Applicant: New Jersey Institute of Technology, Newark, NJ (US)

(72) Inventor: Xuan Liu, Berkeley Heights, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 705 days.

(21) Appl. No.: 15/674,796

(22) Filed: Aug. 11, 2017

(65) Prior Publication Data
US 2018/0042480 A1   Feb. 15, 2018

Related U.S. Application Data (60) Provisional application No. 62/374,992, filed on Aug. 15, 2016.

(51) Int. Cl.
*A61B 5/00* (2006.01)

(52) U.S. Cl.
CPC .......... *A61B 5/0066* (2013.01); *A61B 5/0053* (2013.01); *A61B 2560/0223* (2013.01); *A61B 2562/0233* (2013.01)

(58) Field of Classification Search
CPC ................ A61B 5/0066; A61B 5/0053; A61B 2562/0233; A61B 2560/0223; G01B 2290/25; G01D 5/35312
See application file for complete search history.

(56) References Cited

U.S. PATENT DOCUMENTS

| | | | | |
|---|---|---|---|---|
| 5,076,672 | A * | 12/1991 | Tsuda ................... | G02F 3/00 |
| | | | | 359/244 |
| 7,777,891 | B2 * | 8/2010 | Hasegawa ............ | A61B 5/0059 |
| | | | | 356/485 |

(Continued)

OTHER PUBLICATIONS

Yi Qiu, Yahui Wang, Yiqing Xu, Namas Chandra, James Haorah, Basil Hubbi, Bryan J. Pfister, and Xuan Liu, "Quantitative optical coherence elastography based on fiber-optic probe for in situ measurement of tissue mechanical properties," Biomed. Opt. Express 7, 688-700 (Jan. 26, 2016) (Year: 2016).*

(Continued)

*Primary Examiner* — Serkan Akar
*Assistant Examiner* — Aminah Asghar
(74) *Attorney, Agent, or Firm* — Lerner, David, Littenberg, Krumholz & Mentlik, LLP (57) ABSTRACT

A miniature quantitative optical coherence elastography system with an integrated Fabry-Perot force sensor for in situ elasticity measurement of biological tissue is provided. The technique has great potential for biomechanics modeling and clinical diagnosis. The qOCE system contains a fiber-optic probe that exerts a compressive force to deform tissue at the tip of the probe. Using the space-division multiplexed optical coherence tomography signal detected by a spectral domain optical coherence tomography engine, probe deformation in proportion to the force applied is quantified, as well as the tissue deformation corresponding to the external stimulus. Simultaneous measurement of force and displacement allows for calculation of Young's modulus from the biological tissue. The provided system has had its effectiveness validated on tissue mimicking phantoms, as well as biological tissues, with the advantages of being minimal invasive and also not requiring the use of external agents or substantial pre-measuring preparation.

19 Claims, 7 Drawing Sheets
(6 of 7 Drawing Sheet(s) Filed in Color)

(56) References Cited

U.S. PATENT DOCUMENTS

| | | | |
|---|---|---|---|
| 9,069,130 B2* | 6/2015 | Yun | G01N 21/645 |
| 9,777,053 B2* | 10/2017 | Yun | G01B 9/02091 |
| 2008/0165366 A1* | 7/2008 | Schmitt | G01B 9/02091 |
| | | | 356/519 |

OTHER PUBLICATIONS

Chao Zhou, Aneesh Alex, Janarthanan Rasakanthan, and Yutao Ma, "Space-division multiplexing optical coherence tomography," Opt. Express 21, 19219-19227 (2013) (Year: 2013).*

J. Li et al., "An Optical fibre dynamic instrumented palpation sensor for the characterisation of biological tissue" Sensors and Actuators A 225 (2015) 53-60 (Year: 2015).*

Song et al., "Study of the fiber gin lens tunable Fabry-Perot filter and its application", Proc. SPIE 6150, 2nd International Symposium on Advanced Optical Manufacturing and Testing Technologies: Optical Test and Measurement Technology and Equipment, 61502J (May 19, 2006) (Year: 2006).*

Tarun Kumar Gangopadhyay, "Non-contact vibration measurement based on an extrinsic Fabry-Perot interferometer implemented using arrays of single-mode fibres" 2004 Meas. Sci. Technol. 15 911 (Year: 2004).*

Kelsey, K. M., Kennedy, B. F., McLaughlin, R. A., Sampson, D. D. (2012), "Needle optical coherence elastography for tissue boundary detection" Optics Letters, 37(12), 2310-2312 (Year: 2012).*

Crecea et al., "Magnetomotive nanoparticle transducers for optical rheology of viscoelastic materials", Optics express, 17(25), Dec. 2009, pp. 23114-23122.

Fujimoto et al., "Optical Coherence Tomography: An Emerging Technology for Biomedical Imaging and Optical Biopsy", Neoplasia, vol. 2, Issues 1-2, Jan.-Apr. 2000, pp. 9-25.

Huang et al., "Real-time 3D and 4D Fourier domain Doppler optical coherence tomography based on dual graphics processing units", Biomedical optics express, 3(9), Sep. 2012, pp. 2162-2174.

Izatt et al., "Optical Coherence Tomography for Biodiagnostics", vol. 8, Issue 5, May 1997, p. 41.

Kalanovic et al., "Independent testing of soft tissue visco-elasticity using indentation and rotary shear deformations", Studies in health technology and informatics, Jan. 2003, pp. 137-143.

Kennedy et al., "A review of optical coherence elastography: fundamentals, techniques and prospects", IEEE Journal of Selected Topics in Quantum Electronics, 20(2), Mar. 2014, pp. 272-288.

Kennedy et al., "Analysis of mechanical contrast in optical coherence elastography", Journal of biomedical optics, 18 (12), Dec. 2013, p. 121508.

Kennedy et al., "In vivo three-dimensional optical coherence elastography", Optics express, 19(7), Mar. 2011, p. 6623.

Kennedy et al., "Needle optical coherence elastography for tissue boundary detection", Optics letters, 37(12), Jun. 2012, pp. 2310-2312.

Kennedy et al., "Quantitative micro-elastography: imaging of tissue elasticity using compression optical coherence elastography", Scientific reports, Oct. 2015, 5.

Kennedy et al., "Strain estimation in phase-sensitive optical coherence elastography", Biomedical optics express, 3(8), Aug. 2012, pp. 1865-1879.

Lamouche et al., "Review of tissue simulating phantoms with controllable optical, mechanical and structural properties for use in optical coherence tomography", Biomedical optics express, 3(6), Jun. 2012, pp. 1381-1398.

Li et al., "Quantitative elastography provided by surface acoustic waves measured by phase-sensitive optical coherence tomography", Optics letters, Feb. 15, 2012, 37(4):722-4.

Liang et al., "Biomechanical properties of in vivo human skin from dynamic optical coherence elastography", IEEE Transactions on Biomedical Engineering, 57(4), Apr. 2010, pp. 953-959.

Liang et al., "Dynamic optical coherence elastography: a review", Journal of innovative optical health sciences, Oct. 2010;3(04):221-33.

Liu et al., "Miniature fiber-optic force sensor based on low-coherence Fabry-Pérot interferometry for vitreoretinal microsurgery", Biomedical optics express, May 1, 2012, 3(5):1062-76.

Lorenser et al., "Ultrathin fiber probes with extended depth of focus for optical coherence tomography", Optics letters, May 15, 2012, 37(10):1616-8.

Mao Yet al., "Graded-index fiber lens proposed for ultrasmall probes used in biomedical imaging", Applied optics, Aug. 10, 2007, 46(23):5887-94.

McKee et al., Indentation versus tensile measurements of Young's modulus for soft biological tissues', Tissue Engineering Part B: Reviews, Mar. 10, 2011, 17(3):155-64.

McKnight et al., MR elastography of breast cancer: preliminary results, American journal of roentgenology, Jun. 2002, 178(6):1411-7.

McLaughlin et al., "Imaging of breast cancer with optical coherence tomography needle probes: feasibility and initial results", IEEE Journal of Selected Topics in Quantum Electronics, May 2012, 18(3):1184-91.

Mohan et al., "Elastography of soft materials and tissues by holographic imaging of surface acoustic waves", Optics express, Aug. 13, 2012, 20(17):18887-97.

Nguyen et al., "Visualizing ultrasonically induced shear wave propagation using phase-sensitive optical coherence tomography for dynamic elastography", Optics letters, Feb. 15, 2014, 39(4):838-41.

Samani et al., "Elastic moduli of normal and pathological human breast tissues: an inversion-technique-based investigation of 169 samples", Physics in medicine and biology, Feb. 16, 2007, 52(6):1565.

Schmitt, "OCT elastography: imaging microscopic deformation and strain of tissue", Optics express 3.6, Sep. 1998, pp. 199-211.

Sun et al., "Development and preliminary data of novel integrated optical micro-force sensing tools for retinal microsurgery", InRobotics and Automation, 2009, ICRA'09, IEEE International Conference on May 12, 2009 (pp. 1897-1902). IEEE.

Sun et al., "Optical coherence elastography: current status and future applications", Journal of biomedical optics, Apr. 1, 2011, 16(4):043001-.

Wang et al., "Phase-sensitive optical coherence elastography for mapping tissue microstrains in real time", Applied Physics Letters, 90(16), Apr. 2007, p. 164105.

Wang et al., "Robust motion tracking based on adaptive speckle decorrelation analysis of OCT signal", Biomedical optics express, Nov. 1, 2015, 6(11):4302-16.

Wang et al., "Tissue Doppler optical coherence elastography for real time strain rate and strain mapping of soft tissue", Applied Physics Letters, 89(14), Oct. 2006, p. 144103.

Zhang et al., "Microgap Multicavity Fabry-Perot Biosensor", Journal of lightwave technology, Jul. 1, 2007, 25 (7):1797-804.

Zhao et al., Sapphire ball lens-based fiber probe for common-path optical coherence tomography and its applications in corneal and retinal imaging, Optics letters, Dec. 1, 2012, 37(23):4835-7.

* cited by examiner

MINIATURE QUANTITATIVE OPTICAL COHERENCE ELASTOGRAPHY USING A FIBER-OPTIC PROBE WITH A FABRY-PEROT CAVITY

CROSS-REFERENCE TO RELATED APPLICATION

The present application claims the benefit of the filing date of U.S. Provisional Patent Application No. 62/374,992, filed Aug. 15, 2016, the disclosure of which is hereby incorporated herein by reference.

FIELD OF USE

The present disclosure relates to the field of optical coherence tomography. In particular, the present disclosure relates to the field of optical coherence elastography.

BACKGROUND OF THE INVENTION

Optical coherence tomography ("OCT") is a versatile, high-resolution imaging technique using various different sources of light, typically near-infrared light. OCT has great potential in tissue characterization for various biomedical applications such as cancer diagnosis or surgical guidance, while still being minimally invasive and not requiring any external agents or dyes. OCT can also be used to perform mechanical characterization of biological tissue, referred to as optical coherence elastography ("OCE").

OCE can quantify mechanical response of biological tissues under external or internal mechanical stimulation and extract tissue properties related to the tissue's pathological and physiological status. Some mechanical characterization performed on tissue include: deformation, resonant frequency, and elastic wave propagation. Pathological tissue such as cancerous tissue is usually stiffer compared to normal tissue. This tissue stiffening is exactly what a clinician looks for when he/she examines the tissue for changes in mechanical properties, via ordinary physical examination.

Mechanical compression OCE's superior spatial resolution, mechanical sensitivity, and imaging speed makes it a preferable alternative in tissue study, particularly when compared with elastography techniques based on ultrasound or MRI. Mechanical compression OCE relies on the mechanical compression and subsequent deformation of tissue in order to draw conclusions about the health of the tissue, as compared to prototypical "healthy" tissue.

Surface acoustic wave OCE ("SAW OCE"), and magnetomotive OCE ("MM OCE") are less desirable than compression OCE because SAW OCE has a smaller spatial resolution, while MM OCE requires the use of an external contrasting agent. Compression OCE provides a minimally invasive method of examining tissue for signs of abnormality with higher precision than a conventional physical examination, leading to earlier diagnosis and treatments of cancer and other diseases.

To achieve effective examination of deeper tissue, recently developed fiber-optic probes allow endoscopic OCT imaging despite the small penetration depth of the imaging modality. Needle OCE has been used to measure mechanical response from deep tissue via small probes. Compression OCE based on a miniature fiber optic probe has a great potential for in situ characterization of mechanical properties of biological tissue, since it is not necessary to biopsy the studied tissue, which has the added benefit of reducing chance of skewed measurements as compared with tissue that has been removed.

Currently, Young's modulus can be obtained from atomic force microscopy that studies tissue mechanics at the microscopic through nanoscopic scale, or be obtained from tensile stretching or indentation measurement that studies tissue mechanics at the macroscopic scale. However, these techniques rely on ex vivo tissue specimens that have different mechanical properties of tissue in living organism.

Conventional compression OCE measures tissue displacement under quasi-static compression, but does not quantify mechanical loading, unless the state of stress is established through an inverse elastic or viscoelastic solution to the boundary value problem. For quantitative characterization of tissue stiffness, current compressive OCE without the capability for force quantification has limited significance because results obtained from different compression OCE measurement sessions are qualitative and cannot be correlated in longitudinal or comparison studies. Furthermore, compared to SAW OCE that has a spatial resolution in the order of millimeters and MM OCE that requires an external contrast agent, compression OCE provides the highest spatial resolution for elastography and is based on intrinsic mechanical changes during compression. Therefore, there still exists a critical need for a compression OCE to provide for reliable and quantitative measurement.

SUMMARY OF THE INVENTION

Compared to the above methods the presently disclosed system and technique of the quantitative optical coherence elastography (qOCE) system is significantly different from its predecessors. The qOCE of the present invention simultaneously measures the force/stress exerted on tissue and resultant tissue deformation/strain. In addition, a miniature probe can access deep tissues of interest at multiple locations required for clinical applications; such variations lead to different medical outcomes. Overall, qOCE has great potential in interstitial imaging/sensing for in situ tissue mechanical characterization.

The invention utilizes a novel quantitative optical coherence elastography ("qOCE") system and method that measures tissue elasticity using a miniature probe with integrated force sensing functionality is disclosed. The qOCE system simultaneously measures the force/stress exerted on a tissue sample and the resultant tissue deformation/strain. In addition, the miniature probe can access deep tissues of interest at multiple locations required for clinical applications; such variations lead to different medical outcomes. Overall, qOCE provides for interstitial imaging/sensing for in situ tissue mechanical characterization, while still remaining minimally invasive and not requiring the use of external agents or dyes.

In one embodiment, the qOCE system 10 is comprised of: a fiber-optic probe with an integrated Fabry-Perot cavity, and a spectral domain OCT (optical coherence tomography) engine, which was used to detect space-division multiplexed signal for simultaneous force and displacement measurement. The spectral domain OCT engine is comprised of a spectrometer, a super luminescent diode (SLD), and a reference arm. Signal processing was implemented in real-time using a graphic processing unit (GPU).

The invention may further utilize an axial resolution of the qOCE system limited by the 7.4 µm axial resolution of OCT imaging and the lateral resolution of the qOCE instrument determined by optical confinement of light beam incident into sample. In principle, the qOCE system allows spatially resolved characterization of mechanical property.

A phantom with homogeneous mechanical property was tested using qOCE and spatial resolution for elastography was not the major concern. The qOCE system has great application possibilities, such as cancer diagnosis, brain injury study, tissue engineering, and biomechanical modeling, or just about any field that benefits from a minimally invasive manner of collective mechanical properties of tissue in vivo.

Another embodiment, the quantitative optical coherence elastography (qOCE) system is based on a spectral domain OCT (optical coherence tomography) engine. A miniature probe (qOCE probe) is used to induce compression in the sample. If the sample is mechanically homogeneous, the loading produces uniaxial compression. A lead-in single mode fiber (SMF) is attached to the proximal end of the qOCE probe shaft and a pair of GRIN (graded-index) lenses is attached to the distal end of the probe shaft. The cleaved SMF tip and the proximal surface of the first GRIN lens serve as two end surfaces of a low fineness Fabry Perot (FP) cavity. Incident light from the SLD (super luminescent diode) is reflected by two end surfaces ($E_{fp1}$ and $E_{fp2}$) of the FP cavity due to a discontinuity in refractive index (from glass to air and from air to glass). The common path interference between $E_{fp1}$ and $E_{fp2}$ generates an OCT signal (Ascan, Ip) with a peak located at the depth $L_{fp}$ that equals the FP cavity length. The phase of complex valued OCT signal at $L_{fp}$ changes in proportion to the change in FP cavity length and thus the force exerted at the probe tip. Therefore, tracking Doppler phase shift of the common path OCT signal allows the quantification of probe deformation and force/stress exerted through the probe. On the other hand, the GRIN lens pair also functions as an objective lens to focus the light output from SMF for sample illumination. The backscattered light from the sample ($E_s$) is collected by the fiber optic probe and detected by the spectrometer for OCT imaging. $E_s$ interferes with reference light ($E_r$) provided by the reference arm and generates depth profile of the sample. Depending on the implementation, adjustment of the optical path length of reference arm is done so that the OCT signal from the sample ($I_s$) starts beyond $L_{fp}$. Optical path length is matched by a single model fiber patch cord in reference arm and through coarse and fine adjustment of the position of the collimator in reference arm. This configuration allows spatial division multiplexing of the OCT signal for simultaneous probe deformation ($\Delta L_{probe}$) tracking and tissue deformation ($\Delta L_{sample}$) tracking. Notably, the compound lens or a pair of GRIN lenses allows light beam to be tightly focused into sample and $L_{fp}$ to be small. A shorter FP cavity length allows $I_s$ to be located closer to the equal optical path plane with insignificant signal roll-off. Denote the optical path length (OPL) of light reflected by the distal surface of the second GRIN lens as LGRIN. By choosing the OPL of the reference arm ($L_{ref}$) to be smaller than $L_{GRIN} + L_{fp}$, the sample can be located beyond $L_{fp}$ to eliminate overlap with signal from the FP cavity. Using OCT signals obtained, probe deformation is quantified $\Delta L_{probe}$ and derived is the force exerted: $F = \alpha \Delta L_{probe}$ where $\alpha$ is a constant determined by the mechanical property of the probe and characterized through calibration experiments. The stress applied to the sample is quantified: $\sigma = F/A$ where A is the area of the GRIN lens. In addition, tissue strain is calculated $\varepsilon = \Delta L_{sample}/L_0$. Here, $L_0$ is the initial specimen thickness before compression. Finally, the sample's Young's modulus (E) that is the linear slope of strain-stress curve can be obtained.

Any combination and/or permutation of the embodiments and objects described for a quantitative optical coherence elastography system and method are envisioned and within the scope of the invention. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

One embodiment of a device to measure elasticity of a biological tissue is described below. Specifically, a device and method capable of measuring deformation and force simultaneously on a tissue is discussed. While this embodiment suggests particular materials and methods of construction, it is understood that similar devices to measure mechanical properties of tissue could be created with variations to the disclosed materials and method of construction.

Construction of the qOCE System.

In one embodiment, the quantitative optical coherence elastography system ("qOCE") 10 could include: a qOCE probe and a spectral domain engine. The spectral domain OCT engine could include a reference arm, a super luminescent diode ("SLD"), and a fiber optic coupler ("FC").

Figure 1:
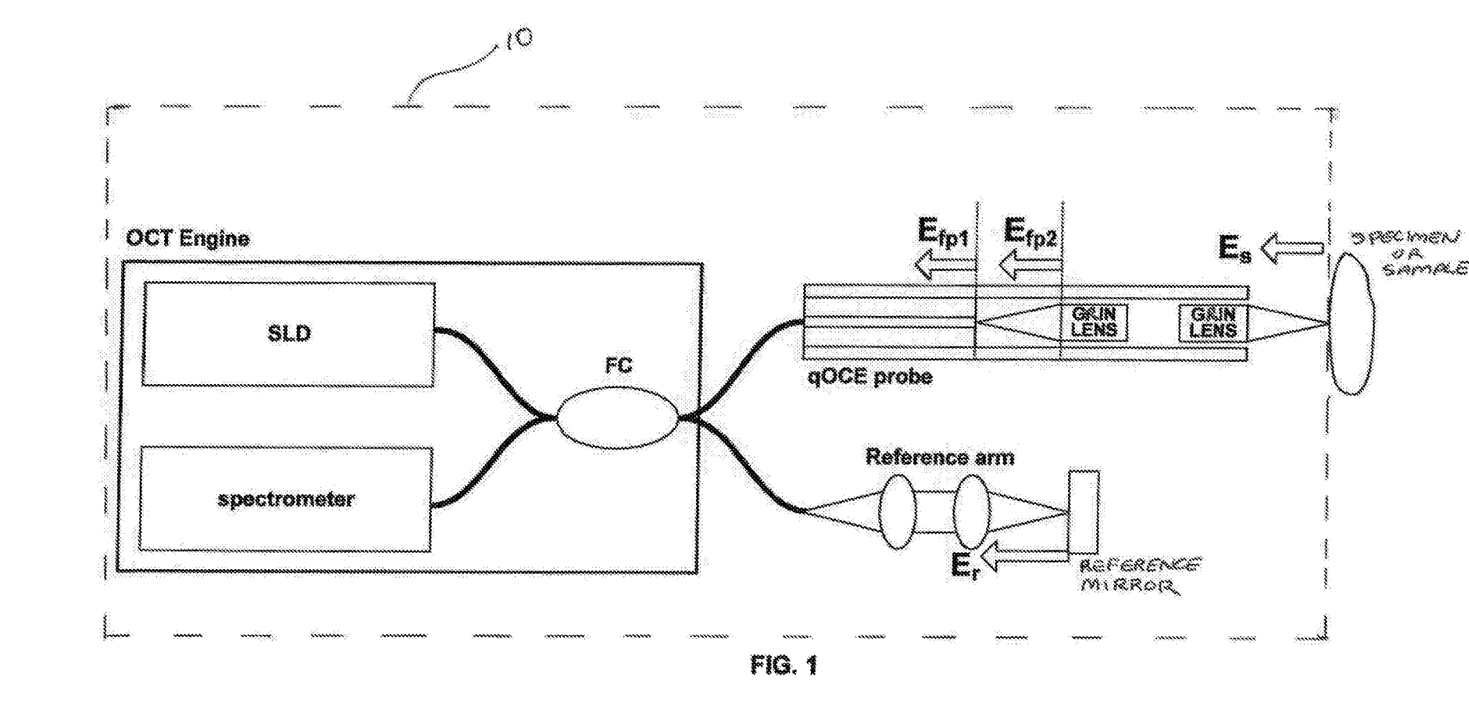
FIG. 1 is an illustration of a qOCE system 10.

FIG. 1 is a schematic for the qOCE system 10. Broadband output from a super luminescent diode is routed by a fiber optic coupler to the qOCE probe and the reference arm. A miniature probe is used to induce compression in a tissue sample. If the sample is mechanically homogeneous, the loading produces uniaxial compression. Otherwise, the state of stress is determined by its heterogeneity, which can also be measured.

FIG. 1 shows a lead-in single mode fiber ("SMF") attached to a proximal end of the qOCE probe shaft and a pair of GRIN lenses is attached to a distal end of the probe shaft. To track probe deformation in response to the applied force, a common-path OCT signal is detected. The common-path OCT signal is derived from the interference from optical fields reflected from the tip of a single mode fiber ("$E_{fp1}$") and from the distal surface of the second gradient index ("GRIN") lens ("$E_{fp2}$"). Another OCT signal derived from the interference between sample light ("$E_s$") and reference light ("$E_r$") through Michelson interferometry is used to track sample deformation in front of the probe tip.

The SMF is inserted into a 25-gauge stainless steel tube in one embodiment. It will be understood that other types of tubes could be used. The fiber and the tube were glued together with optical epoxy to achieve desired rigidity for elasticity measurement. With additional cascaded tubing, the fiber was integrated with a polyimide tube (Microlumen) with 1.8 mm inner diameter. Optical epoxy was applied to the proximal end of the polyimide tube for fixation. It will be understood that the fiber could be integrated with other types of tubes. The size of the tubes could vary.

A pair of 0.23 pitch, 0.26 mm working distance GRIN lenses (Newport) was attached to the distal end of the polyimide tube. Other types of lenses could be utilized. The distance between the first GRIN lens and the tip of the SMF was adjusted to collimate the light beam. The second GRIN lens was used to focus the light beam so that the waist of the output beam was located at a depth 0.26 mm away from the GRIN lens surface in one embodiment. Other suitable depths could have been used. Notably, the mechanically active segment for OCT sensing in this probe is the segment between the fixation points of the SMF and the first GRIN lens.

Figure 3:
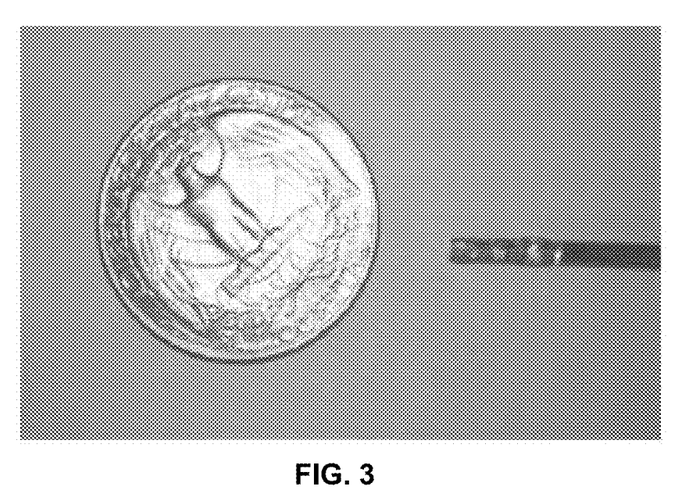
FIG. 3 is a photo of a qOCE probe in comparison with a US quarter.

FIG. 3 shows a qOCE probe in comparison with a US quarter. The cleaved SMF tip and the proximal surface of the first GRIN lens serve as two end surfaces of a low fineness Fabry Perot (FP) cavity.

In one embodiment, the qOCE system uses a 1.3 μm spectral domain ("SD") OCT engine that tracks both probe and sample deformation. A 100 nm bandwidth, super luminescent diode (SLD1325 Thorlabs) corresponding to 7.4 μm axial resolution in OCT imaging is used as a light source. Interference signal used to ultimately measure the length of the FP cavity is detected by a CMOS InGaAs camera (SUI1024LDH2, Goodrich). It will be understood that the sizes of the various components herein could vary.

The GRIN lens pair also functions as an objective lens to focus the light output from the SMF for sample illumination. The backscattered light from the sample ($E_s$) is collected by the fiber optic probe and detected by the spectrometer for OCT imaging. $E_s$ interferes with reference light ($E_r$) provided by the reference arm and generates depth profile of the sample.

The reference arm of the qOCE system will now be described. The optical path length of reference arm is adjusted, so that OCT signal from the sample ($I_s$) starts beyond $L_{fp}$. Optical path length is matched by a single model fiber patch cord in reference arm and through coarse and fine adjustment of the position of the collimator in reference arm. This configuration allows spatial division multiplexing of the OCT signal for simultaneous probe deformation ($\Delta L_{probe}$) tracking and tissue deformation ($\Delta L_{sample}$) tracking. Notably, the compound lens (a pair of GRIN lenses) allows light beam to be tightly focused into sample and $L_{fp}$ to be small.

A shorter FP cavity length allows $I_s$ to be located closer to the equal optical path plane with insignificant signal roll-off. The optical path length ("OPL") of light reflected by the distal surface of the second GRIN lens is denoted as $L_{GRIN}$. By choosing the OPL of the reference arm ("$L_{ref}$") to be smaller than $L_{GRIN}+L_{fp}$, sample can be located beyond $L_{fp}$ to eliminate overlap with signal from the FP cavity. If the material of the specimen (phantom or tissue) is linearly elastic, a static force yields a uniform displacement. If the material is viscoelastic, a dynamic sinusoidal force can be applied and the response measured. Because the mechanical property of the specimen is unknown, a simplified linear elastic model with a Young's modulus E is assumed in the present disclosure.

How the qOCE Generates a Measurement and how that Measurement can be Calculated into the Young Modulus.

The operation of the qOCE system will be described. In the current embodiment, the mechanical load is slowly applied to a tissue sample; therefore, force applied is equivalent to force measured by the integrated Fabry Perot force sensor. Only elastic, and not viscoelastic, samples are considered, although it is contemplated that the apparatus can also measure the mechanical properties of viscoelastic samples with minimal modification. However, almost all of biological tissues are viscoelastic rather than elastic and therefore exhibit time-dependent strain under mechanical loading. Nevertheless, the elastic model for biological tissue is usually valid for small strain (<10%) under quasi-static mechanical loading. In fact, incremental sample deformation and probe deformation ($\delta L_{sample}$ and $\delta L_{probe}$) were quantified over the entire process of compression of qOCE measurement, as shown (Eq (5)). Although only two values, accumulated sample deformation and probe deformation ($\Delta L_{sample}$ and $\Delta L_{probe}$) were involved in elasticity calculation, the qOCE technique developed in the present disclosure has the capability to track the temporal profile of deformation with mechanical stimulation to fully characterize viscoelasticity of biological tissue.

Phantoms were examined in addition to biological tissue to evaluate the effectiveness of the qOCE system. A silicone-based phantom is selected because the elastic modulus of a silicone phantom can be varied in a range that closely overlaps the elastic modulus of biological tissues. The optical property of silicone phantom in terms of refractive index is also close to that of biological tissues. To obtain a phantom with different stiffness, polydimethylsiloxane (PDMS) fluid is combined with the curing agent at different volumetric ratios to simulate different kinds of organic tissue. In addition, titanium dioxide was added into the silicone for light scattering.

Disclosed are results of an experimental trial are based on phantoms and biological tissue that are not compressible and therefore have a Poisson's ratio of 0.5, although it is envisioned that compressible materials may also be measured with minimal modification to the apparatus.

The elastic tissue specimens provided as example samples that the disclosed system is intended to measure are sandwiched by two rigid compressors, one of which is the quantitative coherence elastography probe tip. This configuration provides the most simplified boundary condition and is equivalent to indentation measurement frequently used to characterize biomechanical properties of soft tissue. For example, indentation measurement on Young's moduli of breast tissues was performed through simultaneous quantification of mechanical loading and tissue deformation, but other substances are envisioned to also be measurable, such as collagen, elastin, and keratin.

Incident light from the SLD is reflected by the tip of the SMF and the distal surface of the first GRIN lens ($E_{fp1}$ and $E_{fp2}$) of the FP cavity due to a discontinuity in refractive index between the glass lenses and the empty air-filled space between the lenses. The common path interference between $E_{fp1}$ and $E_{fp2}$ generates an OCT signal (A-scan, $I_p$) with a peak located at the depth $L_{fp}$ that equals the FP cavity length. The phase of complex valued OCT signal at $L_{fp}$ changes in proportion to the change in FP cavity length and thus the force exerted at the probe tip. The CMOS camera detects this OCT signal that is processed in an exemplary manner discussed below to arrive at the length of the FP cavity. Therefore, tracking Doppler phase shift of the common path OCT signal allows the quantification of probe deformation and force/stress exerted through the probe.

The principal accomplishment of the qOCE system is to provide a means to simultaneously quantify force exerted on a sample, as well as its deformation. By tracking changes in the length of the FP cavity, subsequent calculations could be made to determine the force, stress, strain, and deformation of a sample. The means of calculating properties that are not directly measured by the qOCE system are exemplary and are subject to improvement, particularly in light of several assumptions discussed below.

Using OCT signals obtained, probe deformation $\Delta L_{probe}$ may be quantified. Using $\Delta L_{probe}$ the force exerted on the sample: $F = \alpha \Delta L_{probe}$ where $\alpha$ is a constant determined by the mechanical property of the probe and will be characterized through calibration experiments. The stress applied to sample: $\sigma = F/A$ is quantified where A is the area of the GRIN lens. In addition, tissue strain $\varepsilon = \Delta L_{sample}/L_0$ can be calculated. Here, $L_0$ is the initial specimen thickness before compression. Finally, the sample's Young's modulus (E) that is the linear slope of strain-stress curve can be obtained using Equation (1) where tissue elasticity can be quantified by comparing the deformation of probe and sample.

$$E = \frac{\sigma}{\varepsilon} = \frac{\alpha L_0}{A}\left(\frac{\Delta L_{probe}}{\Delta L_{sample}}\right). \quad (1)$$

Notably, Eq (1) is valid based on the following assumptions. First, the load by the qOCE probe is applied slowly. Therefore, force applied to tissue is equivalent to force measured by the integrated Fabry Perot force sensor. Second, the tissue specimen is elastic and viscoelasticity is not considered. Third, the materials are not compressible and therefore have a Poisson's ratio of 0.5.

While mechanical properties of stress and strain are measured by the disclosed apparatus, quantification of other properties is also envisioned with minimal modification. An example of another quantifiable mechanical property of elasticity was also performed using OCT in a similar compression OCE setting.

Figure 6:
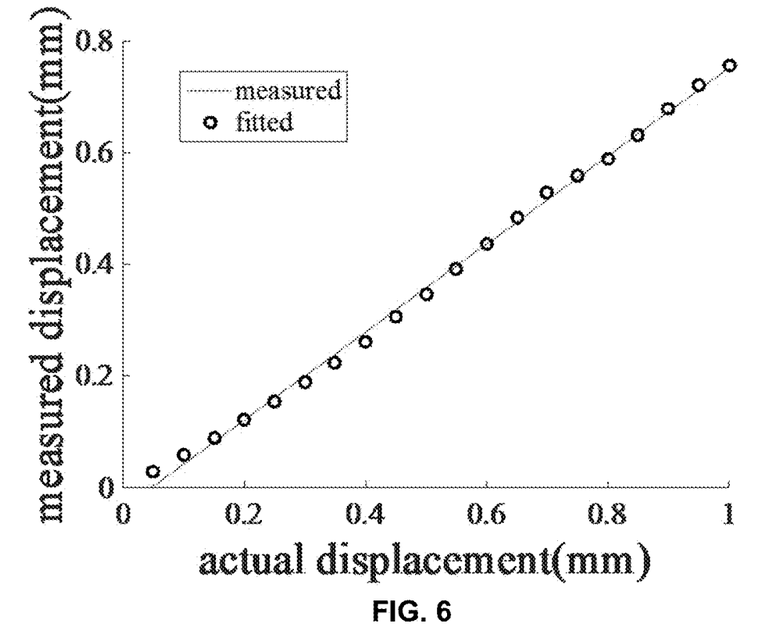
FIG. 6 is a chart illustrating calibration results.

Displacement extracted through Doppler analysis of OCT signal was compared with the known motor displacement, as shown in FIG. 6. Clearly, displacement calculated using Doppler analysis has a linear dependency on actual displacement. $D_{physical} = aD_{Doppler} + b$ was validated as a model using linear regression, and with a=1.2 and b=0.004 mm. $R^2$ statistic of the fitting is 0.9977, indicating a highly linear relationship between the calculated displacement and the actual displacement. The coefficient a accounts for the direction of light propagation and the refractive index of the phantom examined.

Figure 2A:
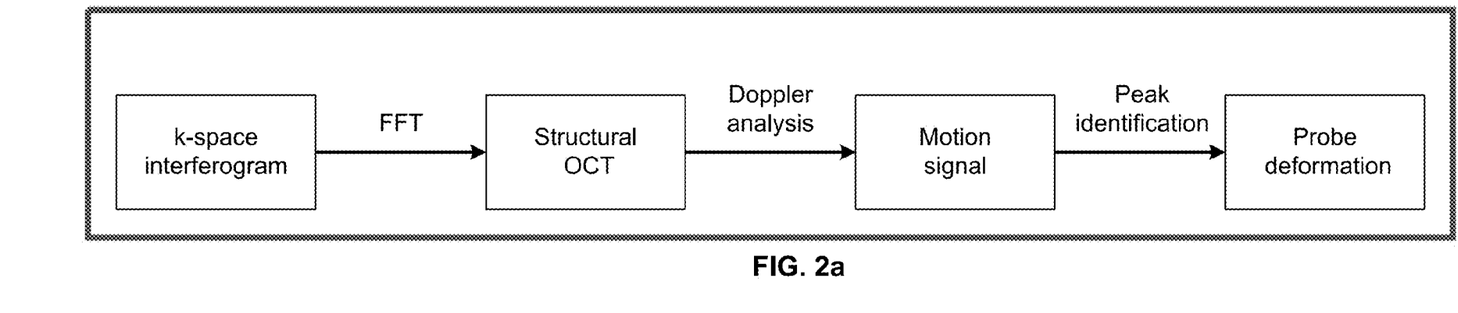
FIG. 2(a) is a flowchart showing signal processing for probe deformation tracking for the quantification of force/stress.
Figure 2B:
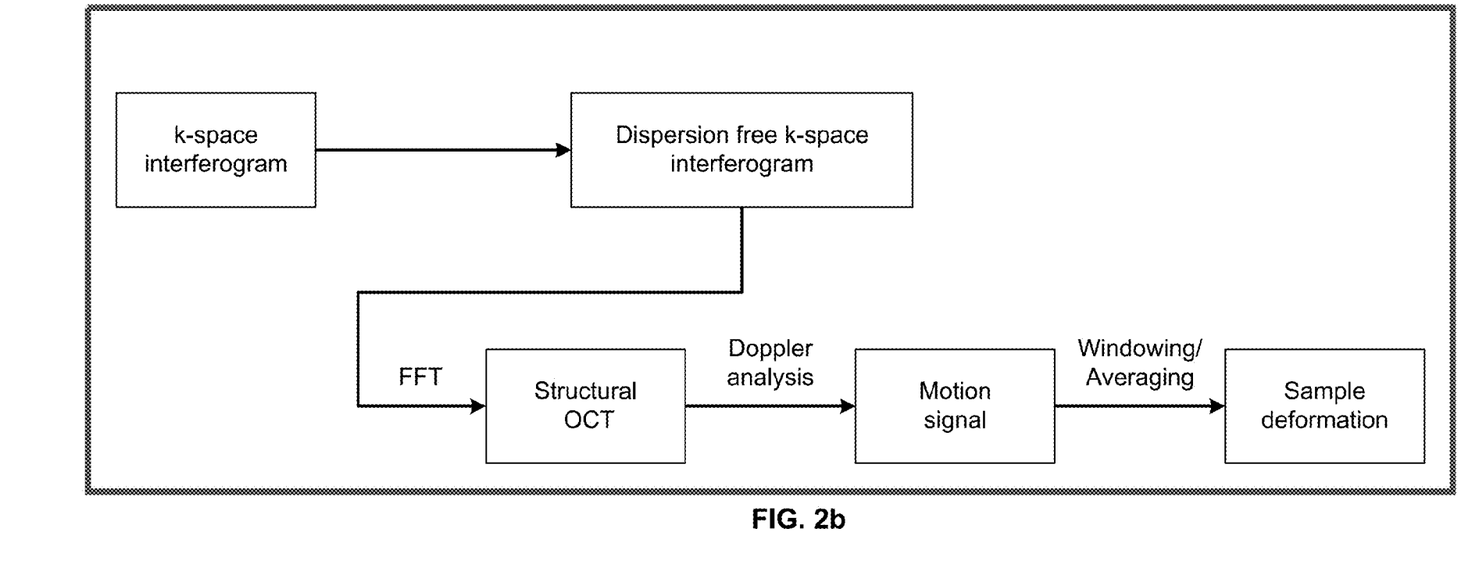
FIG. 2(b) is a flowchart showing signal processing for tissue deformation tracking for the quantification of deformation/strain.

An exemplary signal processing of the OCT signal is provided next. Processing the OCT signal is what allows the eventual quantification of mechanical properties of a sample, as well as increases the reliability of the data, in light of known sources of signal interference. DC subtraction and interpolation is performed on SD OCT data acquired by the CMOS camera to obtain k-space interferograms, where k is the wavenumber. Afterwards, Doppler analysis is performed to track probe and sample deformation. FIGS. 2A and 2B show signal processing applied to track probe deformation and sample deformation, respectively.

FIG. 2A demonstrates signal processing for probe deformation tracking for the quantification of force/stress. A fast Fourier transform on k-space interferogram is performed to obtain a complex valued 1D optical coherence tomography signal $I_p(z,t)$, where z indicates axial coordinate and t indicates measurement time. The signal peak generated by the interference between optical waves is identified from the two end surfaces of the Fabry Perot cavity and is represented as $I_p(L_{probe},t)$. M Doppler phase shift $\delta\phi(t)$ between A-scans acquired at different time with interval $\delta t_p$=5 ms is calculated according to:

$$\delta\phi_{probe}(t) = \text{atan}[I_p(L_{probe}, t+\delta t_p) I_p^*(L_{probe}, t)] \quad (2)$$

where $\delta\phi_{probe}(t)$ is proportional to probe deformation and thus the force applied. Sample deformation tracking is extracted from OCT signal from the sample ($I_s(z,t)$), also through Doppler analysis (FIG. 2 (b)). Notably, signal processing to track sample deformation is slightly different from probe deformation tracking. First, as shown in FIG. 1, OCT signal from the sample derives from light interference between probe arm and reference arm; therefore suffers from signal degradation due to considerable amount of chromatic dispersion.

To obtain high resolution, high signal to noise ratio OCT signal $I_s(z,t)$ from the sample, the amount of dispersion mismatched is measured prior to the measurement of the OCT signal. The non-linear phase of the interferometric spectrum is extracted through Hilbert transformation on interferometric spectrum. Third order polynomial fitting is applied to approximate the non-linear phase: $\Phi(k) = p_3 k^3 + p_2 k^2 + p_1 k + p_0$. The non-linear phase is then subtracted in the GPU based software before FFT for real-time dispersion compensation. Second, biological tissue is less rigid compared to the plastic probe shaft and deforms more.

Therefore, two A-scans acquired with smaller time interval ($\delta t_s$=0.2 ms) for Doppler phase calculation, denoted as Equation 3 below. Deformation obtained through Doppler analysis may suffer from phase wrapping artifact; further, doppler OCT signal from highly scattering sample is inevitably contaminated by speckle noise. To track sample deformation with higher accuracy, a spatial average is performed to obtain filtered phase shift $\delta\phi_{sample,filtered}(t)$ for better accuracy, denoted as Equation 4 below. $\delta\phi_{sample,filtered}(t)$ is proportional to spatially resolved displacement of the sample that can be converted to local deformation and strain.

$$\delta\phi_{sample}(z,t) = \text{atan}[I_s(z, t+\delta t_s) I_s^*(z, t)]. \quad (3)$$

$$\delta\phi_{sample,filtered}(t) = \int_{L_0-\frac{\delta L}{2}}^{L_0+\frac{\delta L}{2}} \delta\phi_{sample}(z,t)dz. \quad (4)$$

With $\delta\phi_{probe}(t)$ or $\delta\phi_{sample,filtered}(t)$ obtained, probe deformation ($\delta L_{probe}$) and sample deformation ($\delta L_{sample}$) can be calculated according to Eq (5). For probe deformation tracking, the central wavelength of SLD output in air ($\lambda_0=1.3$ μm) is used in Eq (5). For sample deformation tracking, the wavelength is corrected by the refractive index ($\lambda=\lambda_0/n$).

$$\delta L_{probe,sample}(t) = \frac{\delta\phi_{probe,sample}(t)}{4\pi}\lambda. \quad (5)$$

Notably, in compression OCE, mechanical loading is applied to tissue in a quasi-static process and it is essential to quantify deformation over the entire course of compression. Therefore, deformation of probe and sample are both integrated over the same time interval, as shown in Eq (6). The time integration also improves signal to noise ratio for elasticity measurement.

$$\Delta L_{probe,sample}(t) = \int_{t_{start}}^{t} \delta L_{probe,sample}(\tau)d\tau. \quad (6)$$

With probe and sample deformation acquired using Eq (5) and (6), tissue elasticity could be quantified using Eq (1). In the real-time software, a variable is constantly updated to calculate the accumulated displacement: $\Delta L_{probe,sample}=\Delta L_{probe,sample}+dL_{probe,sample}$, where $dL_{probe,sample}$ is the incremental displacement. Signal processing for deformation tracking and elasticity sensing is implemented in real-time using a graphic processing unit (GPU).

Figure 4A:
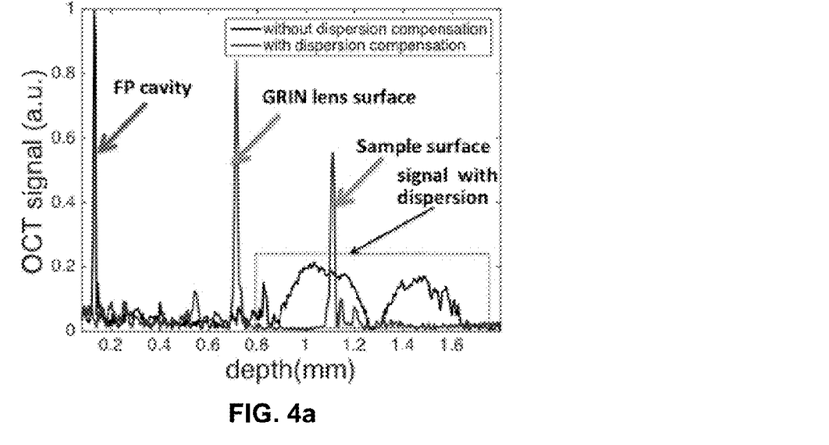
FIG. 4(a) is a chart showing a typical A-scan obtained from the probe without (black) and with (blue) dispersion compensation.

Typical A-scan signals obtained from the qOCE probe are shown in FIG. 4. FIG. 4 (*a*) shows OCT signals obtained from the probe without (solid) and with (dashed) numeric dispersion compensation. The sample was a silicone phantom that used titanium dioxide to provide light scattering. Both A-scans multiplex signals from the common path interferometer and the Michelson interferometer.

For the A-scan obtained without dispersion compensation (solid), a sharp signal peak (arrow) is observed. This peak corresponds to common path OCT signal derived from the FP cavity (interference between optical fields $E_{fp1}$ and $E_{fp2}$ in FIG. 1). As $E_{fp1}$ and $E_{fp2}$ share the same optical path, the interferometric signal is free of dispersion mismatch and a sharp peak is obtained without dispersion compensation. On the other hand, this A-scan shows broadened signal at a larger imaging depth, as indicated by the dashed rectangle in. Signal enclosed by the rectangle derives from the interference between the reference mirror ($E_r$) and the distal surfaces of the second GRIN lens ($E_{GRIN}$), as well as specimen ($E_s$) under imaging. Reference light and sample light in the Michelson interferometer travels in different medium (fiber and air).

Considerable signal degradation is observed because of dispersion mismatch. In comparison, the dashed curve in FIG. 4 (*a*) obtained after dispersion compensation shows a sharp peak corresponding to the distal surface of the GRIN lens (indicated by the arrow), a sharp peak corresponding to the sample surface (indicated by the arrow) and depth resolved sample profile.

However, OCT signal due to interference between $E_{fp1}$ and $E_{fp2}$ diminishes in the dashed curve because of additional non-linear phase induced to dispersion-free signal in the process of numerical dispersion compensation. FIG. 4 (*a*) clearly shows that OCT signal from the Fabry-Perot cavity for force/stress measurement is spatially demultiplexed with OCT signal from tissue for displacement/strain measurement.

Calibrating the qOCE Probe and Reference Arm

An exemplary method of calibrating the qOCE probe is presented in one embodiment. Accurate characterization of elastic property of tissue depends on accurate measurement of externally applied force/stress and the tissue's response in the form of deformation/strain. The accuracy of deformation or displacement tracking is calibrated experimentally. The qOCE probe is attached to a precise linear motor. The qOCE probe is translated by the motor in its axial direction and does not touch the rigid scattering sample. Therefore, the displacement between the probe and the sample was equivalent to the distance translated by the motor. Using OCT signal, displacement between qOCE probe and sample is calculated according to Eq (3)-(6), using real-time GPU software.

Displacement extracted through Doppler analysis of OCT signal was compared with the known motor displacement, as shown in FIG. 6. Clearly, displacement calculated using Doppler analysis has a linear dependency on actual displacement. The following model $D_{physical}=aD_{doppler}+b$ using linear regression was validated, and the results of the present disclosure indicated a=1.2 and b=0.004 mm $R^2$ statistic of the fitting is 0.9977, indicating a highly linear relationship between the calculated displacement and the actual displacement. The coefficient a accounts for the direction of light propagation and the refractive index of the phantom.

Figure 7:
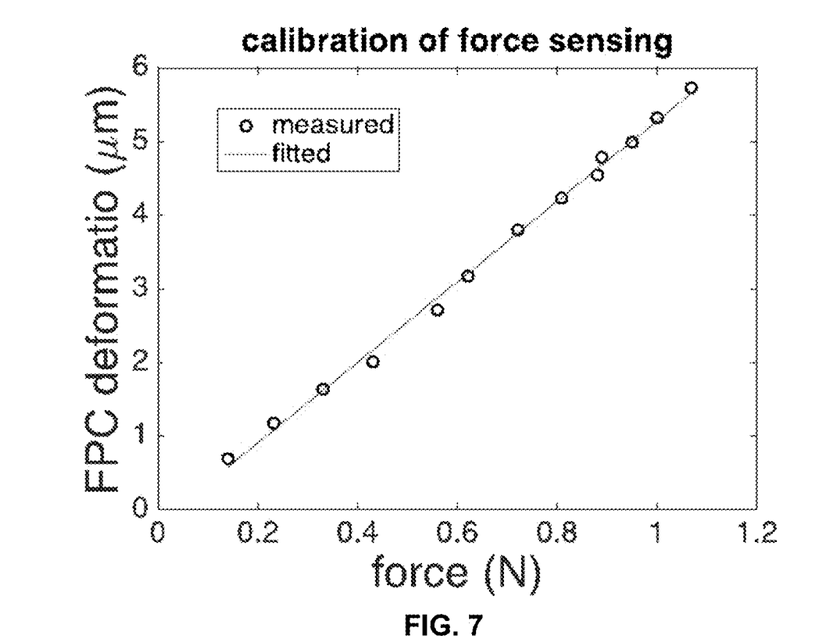
FIG. 7 is a chart illustrating results of force calibration show FP cavity deforms proportionally to force exerted; and, FIG. 8 is a chart illustrating stress-strain curve obtained using qOCE measurement (dashed) and calibration of strain-stress curve (solid).

The force/stress sensing capability of the qOCE system could also be calibrated via the exemplary described method. The qOCE is mounted on a linear stage and the whole stage is translated to exert force to the sensing tip of a digital force gauge, which provides high precision force measurement with a 0.005 N resolution. qOCE probe deformation is tracked using a Doppler OCT signal obtained from the integrated Fabry-Perot cavity and is compared with the probe deformation with force exerted, as shown in FIG. 7. The length of the Fabry-Perot cavity varied linearly with the force. $D_{FPC}=\alpha F+\beta$ as a model was validated using linear regression, and the results of the present disclosure indicated $\alpha=0.1795$ N/μm. $R^2$ statistic of the fitting is 0.9971, indicating a highly linear relationship between the force and the probe deformation.

FIGS. 6 and 7 illustrate that the force and displacement can be quantified using OCT signal. FIG. 6 shows calibration results that show displacement obtained from Doppler OCT signal that is linearly related to actual displacement. FIG. 7 shows results of force calibration that show FP cavity deforms proportionally to the force exerted. Based on results obtained from the calibration experiments, the phase shift extracted from OCT signal to tissue deformation and force was converted. Stress was then calculated using the area of the GRIN lens (~2.54 mm$^2$) in contact with sample for compression.

Optical path length is matched by a single model fiber patch cord in the reference arm and through coarse and fine adjustment of the position of the collimator in the reference arm. This configuration allows spatial division multiplexing of the optical coherence tomography signal for simultaneous probe deformation tracking and tissue deformation tracking. By choosing the optical path length of the reference arm to be smaller than the sum of optical path length of light reflected by the distal surface of the second GRIN lens, with the depth length of the peak generated by the optical coherence tomography signal, the tissue sample can be located beyond the depth length to eliminate overlap with signal from the Fabry Perot cavity.

A polyimide tube is used as a qOCE probe shaft and assumed it deforms proportionally to force applied. The assumption was validated in the experimental results shown in FIG. 7. Alternatively, superelastic Nitinol could be used that returns to its original shape when loading is released as the material for qOCE probe shaft.

Results

Figure 4B:
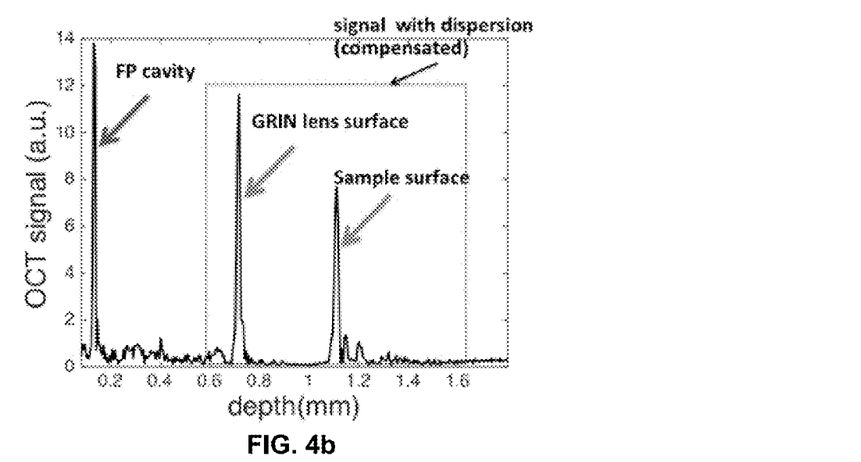
FIG. 4(b) is a chart showing multiplexed signal for simultaneous probe and tissue deformation tracking.
Figure 4C:
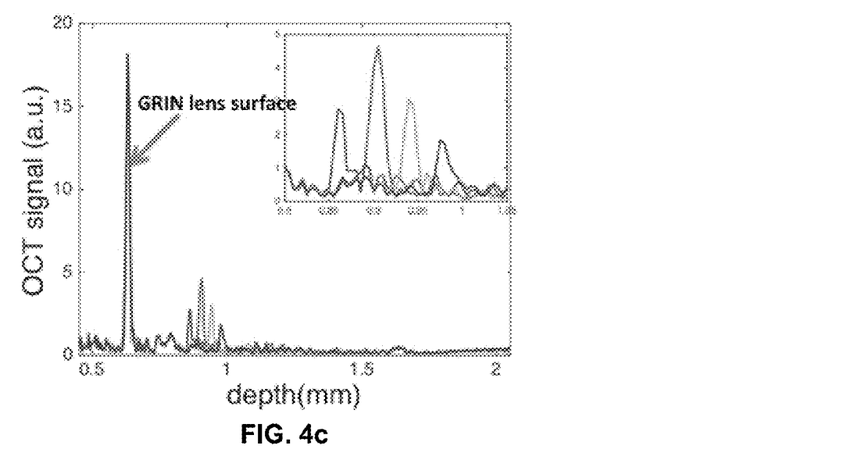
FIG. 4(c) is a chart showing segments of OCT signal obtained from Michelson interferometry after dispersion compensation, with weakly scattered sample located at different depth.

CP OCT signal obtained from the FP cavity was multiplexed without dispersion compensation, and Michelson OCT signal obtained from tissue with dispersion compensation and show the result in FIG. 4 (b). By tracking phase shift between complex valued, spatial division multiplexed OCT signal as shown in FIG. 4 (b), probe and tissue deformation could be quantified. FIG. 4(c) shows segments of OCT signal obtained from the Michelson interferometer after dispersion compensation, with weakly scattering phantom as sample. Different curves were obtained when the sample was located at different depths. Signal peak derived from the GRIN lens surface (indicated by the green arrow) remains identical for different signals. Notably, focusing effect can be observed in FIG. 4 (c) with focal plane approximately 0.26 mm away from the GRIN lens surface.

Figure 5A:
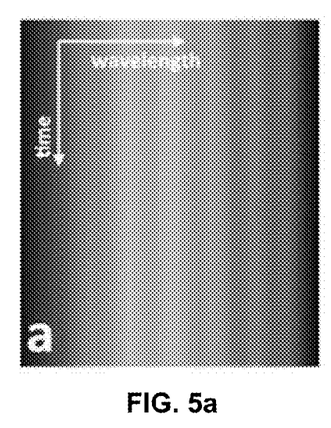
FIG. 5(a) shows a frame of interferometric spectrum obtained when the probe was used to exert force.

To track probe and tissue deformation, temporal variation of A-scan in Doppler phase shift was quantified as shown in FIG. 5. FIG. 5A shows a frame of sequentially acquired spectral interferograms. Different coordinates in horizontal direction correspond to different wavelength/wavenumber and different coordinates in vertical direction correspond to different time. Fringes due to the interference between optical fields from the two end surfaces of the FP cavity are visible in FIG. 5A. As the probe was used to compress tissue during the acquisition of FIG. 5A, slight fringe shift over time can be observed due to probe shaft deformation.

Figure 5B:
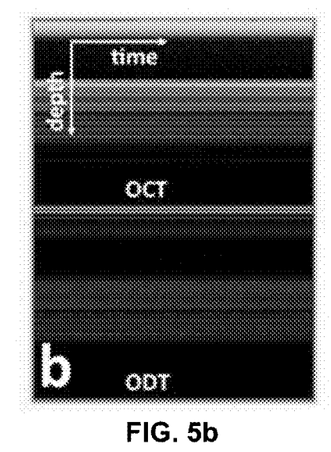
FIG. 5(b) shows structural OCT image (upper) and Doppler OCT image (lower) obtained when the phantom was compressed by the qOCE probe.

FIG. 5A shows a quantified phase shift, using real-time GPU software and Equation 2 to convert the phase shift to probe deformation using Equation 4 and Equation 5. FIG. 5B shows signal from tissue (screen capture of real-time display) when the qOCE probe was used to compress the phantom. The software of the present disclosure showed structural OCT signal, as well as Doppler OCT signal obtained by calculating inter A-scan signal phase shift. Sequentially acquired signals are displayed in FIG. 5B where different coordinates in horizontal direction correspond to different time and different coordinates in vertical direction correspond to different depths.

Figure 5C:
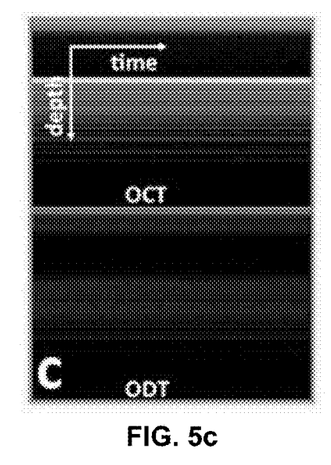
FIG. 5(c) shows structural OCT image (upper) and Doppler OCT image (lower) obtained when the compression was released.

FIG. 5C is the screen capture of real-time display when releasing the compression exerted to the same phantom through the probe. Notably, in the software, the color of Doppler signal was used to identify the direction of the motion or phase shift. The negative phase shift was coded to be red and the positive phase shift was coded to be blue. Due to small time window (0.1 s) for the acquisition of A-scans during quasi-static compression shown in FIGS. 5B and 5C, phantom deformation was small and could not be observed in structural OCT images. However, the phase of OCT signal provides much higher sensitivity in deformation tracking. Deformation of phantom in different directions due to compression and removal of compression could be clearly observed in FIGS. 5B and 5C.

The accuracy of qOCE measurement depends on the effectiveness of Doppler phase analysis in the quantification of force and sample deformation. The minimal displacement between A-scans that could be tracked using Doppler phase shift in the current OCT system was approximately 0.1 nm, determined by random phase noise. The maximum displacement between A-scans that could be tracked using Doppler phase shift in the current OCT system was approximately 325 nm, limited by the range free of phase wrapping artifacts. In the present disclosure, the time interval was strategically calculated between A-scans involved in Doppler phase calculation to track phase shifts during the process of quasi-static compression. The sensitivity of the present device in force measurement could be higher than 0.25 mN and the maximum force applied through the qOCE probe was approximately 1N.

The instrument is limited by the time derivative of force (dF/dt). Doppler analysis of OCT signal essentially quantifies the change of force (dF) within a small time interval (dt). Force is then obtained by integrating dF over time. The accuracy of force measurement is compromised, when dF is large and results in phase wrapping artifacts in Doppler OCT signal. Based on the stiffness of the probe shaft and the imaging speed of the OCT system, the system can theoretically quantify force with a 12,000 N/s derivative. It is possible to adaptively choose A-scans for Doppler phase analysis to improve the robustness in deformation tracking, in a way similar to adaptive speckle tracking method developed before for lateral motion tracking.

Corroborating Calculations with Experimental Trials

To validate that the qOCE can simultaneously quantify stress and strain for elasticity measurement, the qOCE probe was used to compress an elastic phantom. Stress was obtained in real-time using FP cavity deformation extracted from the Doppler phase shift between OCT A-scans, calibrated force-deformation relationship, and known GRIN lens dimension. The phantom strain was obtained in real-time, using the OCT signal within a window (approximately 280 μm width) located in the vicinity of beam waist (approximately 260 μm from the surface of the second GRIN lens). Tissue deformation was obtained by averaging the displacement signal obtained through Doppler analysis within the window and corrected by the refractive index of the silicone phantom (n=1.4). Strain was then calculated by dividing the deformation at each depth position and then averaged. The stress and strain values were recorded during the compression of the probe, shown as the black curve in FIG. 8. In addition, the strain stress measurement was repeated, quantifying the force/stress with a commercial force gauge and quantifying the deformation/strain with the accurate linear translation stage.

Figure 8:
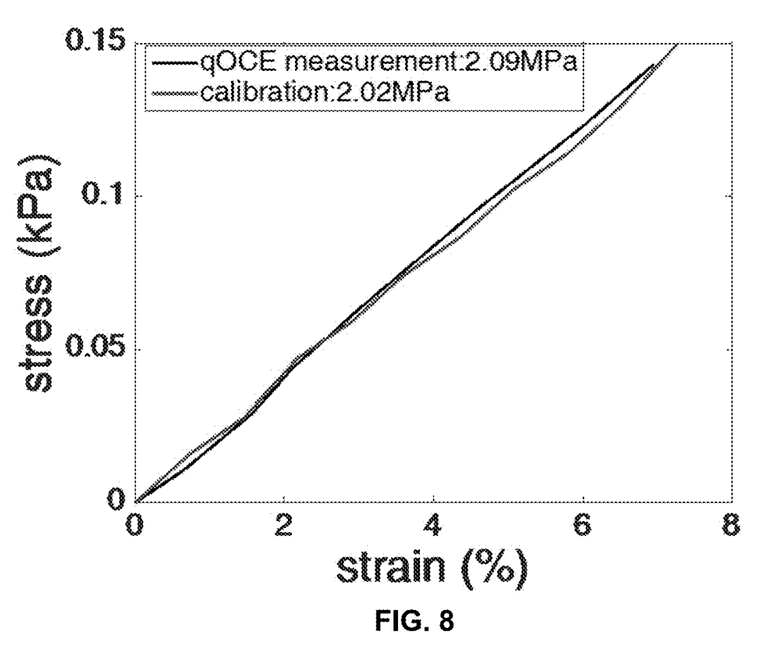

The results obtained in FIG. 8 show that the red calibration curve is highly consistent with qOCE measurement. Phantom elasticity was then obtained according to stress-strain curves shown in FIG. 8. The red curve results in an elasticity modulus that is 2.09 MPa and the black curve results in an elasticity modulus that is 2.02 MPa, indicating high accuracy qOCE measurement of tissue elasticity.

To demonstrate that the qOCE technique developed in the present disclosure can be used to differentiate sample with different stiffness, three PDMS phantoms were fabricated to have different elastic moduli and performed qOCE measurement. The real-time software tracked probe and sample deformation using OCT signal, and used Eq (1) to calculated sample elasticity moduli. Results are shown in Table 1. In addition, calibration experiments were performed for elasticity measurement, shown as the second row of Table 1. In these calibration experiments, force/stress was measured using the force gauge and deformation/strain was obtained according to the reading of the linear stage. Table 1 indicates qOCE can provide reliable elasticity measurement.

TABLE 1

Elasticity measurement on phantom

| Young's modulus | Phantom1 | Phantom2 | Phantom3 |
|---|---|---|---|
| qOCE measurement (MPa) | 0.72 | 0.99 | 2.51 |
| Calibration (MPa) | 0.69 | 0.94 | 2.45 |

The qOCE technique was further validated on biological tissue, by measuring different tissues from chicken (ex vivo). The elasticity of fat, muscle and heart of chicken was compared. The Young's moduli obtained using qOCE are shown in Table 2. The difference in stiffness between different tissues is shown, suggesting the qOCE technique of the present disclosure has the potential in distinguishing cancer tissue from normal tissue. However, it is challenging to correlate results shown in Table 2 with values of Young's moduli reported in literature. This is because reliable data on Young's moduli of soft tissue are very limited and available values tend to be inconsistent.

TABLE 2

Elastic property measurement on chicken tissues

| | Fat | Muscle | Heart |
|---|---|---|---|
| Young's modulus (Mpa) | 0.21 | 0.63 | 7 |

A review study indicated that measured Young's moduli for any given tissue usually span several orders of magnitude. For example, the Young's modulus of breast tissue has an average value of ~7 kPa when measured by atomic force microscopy (AMF) but has an average value of ~480 Mpa when measured by tensile stretching. Notably, Young's moduli obtained from qOCE measurement are generally larger than values obtained from AFM and smaller than values obtained through tensile stretching. This may be due to the tissue volume that qOCE characterizes is larger than the one in AFM measurement and smaller than the one in tensile stretching measurement.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

What is claimed is:

1. A method of quantitative optical coherence elastography (qOCE), comprising:
utilizing a quantitative optical coherence elastography (qOCE) system defined miniature by insertion into a 1.8 mm inner diameter tube; the system having a qOCE fiber-optic probe having an integrated Fabry-Perot (FP) cavity and a pair of GRIN lenses attached to a distal end of the probe;
inducing compression to deform a biological tissue by a force applied by a probe tip of the qOCE fiberoptic probe arranged on the system, the probe having the FP cavity where incident light from a super luminescent diode (SLD) is reflected by a pair of fixed reflective surfaces or end facets ($E_{fp1}$ and $E_{fp2}$) in the integrated FP cavity, wherein common path interference between $E_{fp1}$ and $E_{fp2}$ generates a common path optical coherence tomography (OCT) signal;
using the common path (OCT) signal detected by a spectral domain OCT engine to quantify the probe deformation that is proportional to the force applied, wherein the spectral domain OCT engine includes a spectrometer, the super luminescent diode (SLD), and a reference arm;
collecting a backscattered light from the biological tissue under compression using the GRIN lenses that focus a light output from a single mode fiber (SMF) attached to a proximal end of the qOCE fiber optic probe for biological tissue illumination, wherein the backscattered light from the biological tissue is combined with a reference light that is provided by a reference mirror ($E_r$) in a fiber-optic Michelson interferometer for a Michelson OCT signal, and using the Michelson OCT signal for biological tissue imaging and deformation tracking;
using an optical path length (OPL) of the reference arm chosen in size to eliminate overlap with the common path OCT signal from the FP cavity, and detecting both the common path OCT signal and the Michelson OCT signal with the spectrometer from both a common path interferometer and from the Michelson interferometer simultaneously and spatially demultiplexed;
wherein force sensing is derived from interference between optical fields reflected by the end facets of the FP cavity at the probe tip, and wherein biological tissue imaging is derived from the biological tissue and the reference arm; and
measuring simultaneously the force and displacement of the biological tissue to extract Young's modulus of the biological tissue.

2. The method of claim 1, further includes quantifying the biological tissue deformation corresponding to the external stimulus.

3. The method of claim 1, further includes calibrating the qOCE system.

4. The method of claim 1, further includes using the qOCE system for clinical diagnosis.

5. The method of claim 1, further includes using the qOCE system for biomechanics modeling.

6. The method of claim 1 further includes obtaining in situ elasticity measurement of the biological tissue.

7. The method of claim 6, wherein the biological tissue is soft tissue.

8. The method of claim 7, wherein the soft tissue is deep tissue selected from the group consisting of breast tissue, skin, brain tissue, muscles, tendons, ligaments, connective tissue, lung tissue, liver tissue, kidney tissue, intestinal tissue, stomach tissue, heart tissue, bladder tissue, pancreatic tissue, spleen tissue, and any combination thereof.

9. A quantitative optical coherence elastography system ("qOCE"), comprising,
a quantitative optical coherence elastography (qOCE) system defined miniature by a 1.8 mm inner diameter tube; the system having a qOCE fiber-optic probe having an integrated Fabry-Perot cavity and a pair of GRIN lenses attached to a distal end of the probe;

a probe tip of the qOCE fiberoptic probe arranged on the system for applying a force to induce compression to deform a biological tissue, the probe having the integrated Fabry-Perot cavity where incident light from a super luminescent diode (SLD) is reflected by a pair of fixed reflective surfaces or end facets ($E_{fp1}$ and $E_{fp2}$) in the integrated Fabry-Perot (FP) cavity, wherein common path interference between $E_{fp1}$ and $E_{fp2}$ generates a common path optical coherence tomography (OCT) signal;

a spectral domain OCT engine for detecting the common path (OCT) signal and to quantify a probe deformation that is proportional to the force applied, wherein the spectral domain OCT engine includes a spectrometer, the super luminescent diode (SLD), and a reference arm;

wherein, the GRIN lenses for collecting a backscattered light from the biological tissue under compression, and the GRIN lenses focus a light output from a single mode fiber (SMF) attached to a proximal end of the qOCE fiber optic probe for biological tissue illumination, wherein the backscattered light from the biological tissue is combined with a reference light that is provided by a reference mirror ($E_r$) in a fiber-optic Michelson interferometer for a Michelson OCT signal, and using the Michelson OCT signal for biological tissue imaging and deformation tracking;

an optical path length (OPL) of the reference arm chosen in size to eliminate overlap with the common path OCT signal from the FP cavity, and for detecting both the common path OCT signal and the Michelson OCT signal with the spectrometer from both a common path interferometer and from the Michelson interferometer simultaneously and spatially demultiplexed;

wherein force sensing is derived from interference between optical fields reflected by the end facets of the FP cavity at the probe tip, and wherein biological tissue imaging is derived from the biological tissue and the reference arm; and wherein the force and displacement of the biological tissue is measured simultaneously to extract Young's modulus of the biological tissue.

10. The system of claim 9, wherein the spectral domain OCT engine further includes a fiber optic coupler ("FC").

11. The system of claim 10, wherein broadband output from the SLD is routed by the FC to the qOCE probe and the reference arm.

12. The system of claim 9, wherein the pair of GRIN lenses includes a first set and a second set of gradient index ("GRIN") lenses attached to the distal end of the probe.

13. The system of claim 12, wherein a cleaved SMF tip, and a proximal surface of the first GRIN lens serve as end surfaces of the Fabry Perot ("FP") cavity.

14. The system of claim 12, wherein the common-path OCT signal is derived from interference from optical fields reflected from a tip of the single mode fiber (SMF) of the probe, and from the second set of gradient index ("GRIN") lens defining a distal surface.

15. The system of claim 14, wherein tracking doppler phase shift of the common-path OCT signal allows quantification of the probe deformation, and force exerted through the probe.

16. The system of claim 9, wherein the spectral domain OCT engine is a 1.3 μm spectral domain OCT engine that tracks both probe and sample deformation.

17. The system of claim 9, wherein the super luminescent diode ("SLD") includes a 100 nm bandwidth corresponding to 7.4 μm axial resolution in OCT imaging and used as a light source.

18. The system of claim 9, further includes a complementary metal-oxide semiconductor (CMOS) indium gallium arsenide (InGaAs) camera for detecting an interference signal used to measure the length of the FP cavity.

19. The system of claim 9, wherein the probe deformation from compression is detected with the common-path OCT signal.

* * * * *